United States Patent
Quick et al.

(10) Patent No.: US 8,103,354 B2
(45) Date of Patent: *Jan. 24, 2012

(54) SYSTEMS AND METHODS FOR DETERMINING A THRESHOLD CURRENT LEVEL REQUIRED TO EVOKE A STAPEDIAL MUSCLE REFLEX

(75) Inventors: Andrew P. Quick, Valencia, CA (US); Leonid M. Litvak, Los Angeles, CA (US); Aniket Saoji, Northridge, CA (US)

(73) Assignee: Advanced Bionics, LLC, Valencia, CA (US)

( * ) Notice: Subject to any disclaimer, the term of this patent is extended or adjusted under 35 U.S.C. 154(b) by 522 days.

This patent is subject to a terminal disclaimer.

(21) Appl. No.: 12/236,961

(22) Filed: Sep. 24, 2008

(65) Prior Publication Data

US 2009/0018616 A1 Jan. 15, 2009

Related U.S. Application Data

(63) Continuation-in-part of application No. 11/779,265, filed on Jul. 17, 2007, now Pat. No. 7,925,355.

(60) Provisional application No. 60/831,709, filed on Jul. 17, 2006.

(51) Int. Cl.
  *A61B 1/10* (2006.01)
(52) U.S. Cl. .................. 607/57; 607/55; 607/56
(58) Field of Classification Search ........... 607/55–57
  See application file for complete search history.

(56) References Cited

U.S. PATENT DOCUMENTS

| | | | |
|---|---|---|---|
| 4,400,590 A | 8/1983 | Michelson | |
| 4,532,930 A | 8/1985 | Crosby et al. | |
| 4,592,359 A | 6/1986 | Galbraith | |
| 4,819,647 A | 4/1989 | Byers et al. | |
| 4,947,844 A | 8/1990 | McDermott | |
| 5,015,224 A | 5/1991 | Maniglia | |
| 5,594,174 A | 1/1997 | Keefe | |
| 5,782,744 A | 7/1998 | Money | |
| 5,792,073 A | 8/1998 | Keefe | |
| 5,814,095 A | 9/1998 | Muller et al. | |
| 5,824,022 A | 10/1998 | Zilberman et al. | |
| 6,129,753 A | 10/2000 | Kuzma | |
| 6,157,861 A * | 12/2000 | Faltys et al. .......... | 607/57 |
| 6,205,360 B1 | 3/2001 | Carter et al. | |
| 6,219,580 B1 | 4/2001 | Faltys et al. | |
| 6,272,382 B1 | 8/2001 | Faltys et al. | |

(Continued)

OTHER PUBLICATIONS

Feeney, M. P., et al., "Detection of the Acoustic Stapedius Reflex in Infants Using Wideband Energy Reflectance and Admittance", *J Am Acad Audio* 16:278-290, (2005).

(Continued)

*Primary Examiner* — Niketa Patel
*Assistant Examiner* — Rex R Holmes
(74) *Attorney, Agent, or Firm* — AdvantEdge Law Group, LLC (57) ABSTRACT

Exemplary cochlear implant systems include an implantable cochlear stimulator configured to be implanted within a patient and generate a stimulation current having an adjustable current level, one or more electrodes communicatively coupled to the stimulator and configured to apply the stimulation current to one or more locations within an ear of the patient, and a probe configured to acquire sound data used to derive an acoustic reflectance of the ear. The implantable cochlear stimulator is configured to adjust the current level of the stimulation current until a change in the acoustic reflectance above a threshold is detected.

20 Claims, 9 Drawing Sheets

U.S. PATENT DOCUMENTS

| | | |
|---|---|---|
| 6,308,101 B1 | 10/2001 | Faltys et al. |
| 6,415,185 B1 | 7/2002 | Maltan |
| 6,496,734 B1 | 12/2002 | Money |
| 6,554,762 B2 | 4/2003 | Leysieffer |
| 6,728,578 B1 | 4/2004 | Voelkel |
| 6,879,860 B2 | 4/2005 | Wakefield |
| 6,925,332 B2 | 8/2005 | Franck |
| 6,996,438 B1 | 2/2006 | Voelkel |
| 7,039,466 B1 | 5/2006 | Harrison et al. |
| 7,043,303 B1 | 5/2006 | Overstreet |
| 7,117,038 B1 * | 10/2006 | Overstreet ............ 607/57 |
| 2006/0178711 A1 | 8/2006 | Patrick et al. |

OTHER PUBLICATIONS

International Search Report and Written Opinion in International Application No. PCT/US2008/58830, Aug. 26, 2008.

Non-Final Office Action in U.S. Appl. No. 11/779,265 dated Apr. 2, 2010.

Final Office Action in U.S. Appl. No. 11/779,265 dated Sep. 16, 2010.

* cited by examiner

SYSTEMS AND METHODS FOR DETERMINING A THRESHOLD CURRENT LEVEL REQUIRED TO EVOKE A STAPEDIAL MUSCLE REFLEX

RELATED APPLICATIONS

The present application is a continuation-in-part application of U.S. application Ser. No. 11/779,265, filed Jul. 17, 2007, now U.S. Pat. No. 7,925,355 which application was allowed on Dec. 10, 2010 and claims the benefit of U.S. Provisional Patent Application No. 60/831,709, filed Jul. 17, 2006. Both applications are incorporated herein by reference in their respective entireties.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems seek to bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. A sound processor processes and translates an incoming sound into electrical stimulation pulses applied by these electrodes which directly stimulate the auditory nerve.

When a cochlear implant system is initially implanted in a patient, and during follow-up tests and checkups thereafter, it is usually necessary to fit the cochlear implant system to the patient. Such "fitting" includes adjustment of the base amplitude or intensity of the various stimuli generated by the cochlear implant system from the factory settings (or default values) to values that are most effective and comfortable for the patient. For example, the intensity or amplitude and/or duration of the individual stimulation pulses provided by the cochlear implant system may be mapped to an appropriate dynamic audio range so that the appropriate "loudness" of sensed audio signals is perceived. That is, loud sounds should be sensed by the patient at a level that is perceived as loud, but not painfully loud. Soft sounds should similarly be sensed by the patient at a level that is soft, but not so soft that the sounds are not perceived at all.

Hence, fitting and adjusting the intensity of the stimuli and other parameters of a cochlear implant system to meet a particular patient's needs requires the determination of a most comfortable current level (M). The most comfortable current level refers to a stimulation current level applied by a cochlear implant system at which the patient is most comfortable. The most comfortable current level (M) typically varies from patient to patient and from channel to channel in a multichannel cochlear implant.

Heretofore, the most comfortable current level (M) has been determined by an expert clinician presenting various stimuli to the patient and relying on subjective feedback from the patient as to how such stimuli are perceived. Such subjective feedback typically takes the form of either verbal (adult) or non-verbal (child) feedback. Unfortunately, relying on subjective feedback in this manner is difficult, particularly for those patients who may have never heard sound before and/or who have never heard electrically-generated "sound". For young children, the problem is exacerbated by a short attention span, as well as difficulty in understanding instructions and concepts, such as high and low pitch, softer and louder, same and different. Moreover, many patients, such as infants and those with multiple disabilities, are completely unable to provide subjective feedback.

In addition, the optimal fitting parameters of a cochlear implant system may vary during a patient's lifetime. For example, in the developing nervous system of young children, frequent changes in the intensity of the stimuli may be required in order to optimize the cochlear implant system. The optimal fitting parameters may vary during a woman's menstrual cycle, or may vary with medication or illness. These changes may require frequent refitting sessions.

SUMMARY

Exemplary cochlear implant systems include an implantable cochlear stimulator configured to be implanted within a patient and generate a stimulation current having an adjustable current level, one or more electrodes communicatively coupled to the stimulator and configured to apply the stimulation current to one or more locations within an ear of the patient, and a probe configured to acquire sound data used to derive an acoustic reflectance of the ear. The implantable cochlear stimulator is configured to adjust the current level of the stimulation current until a change in the acoustic reflectance above a threshold is detected.

Exemplary methods of determining a threshold current level required to evoke a stapedial muscle reflex within a patient include applying a stimulation current having an adjustable current level to one or more locations within an ear of a patient, measuring with a fitting station an acoustic reflectance within the ear during the application of the stimulation current, adjusting the current level of the stimulation current until a change in the acoustic reflectance above a threshold is detected, and setting the threshold current level to a value related to the current level of the stimulation current that causes the change in the measured acoustic reflectance.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Systems and methods for detecting stapedial muscle reflex are described herein. An implantable cochlear stimulator is configured to be implanted within a patient and to apply a stimulation current having an adjustable current level via one or more electrodes to one or more locations within an ear of the patient. A probe is configured to acquire sound data used to derive an acoustic reflectance of the patient's ear during the stimulation. By varying the current level of the stimulation current and analyzing the resulting change in the measured acoustic reflectance, the presence of the stapedial muscle reflex may be detected. As will be described in more detail below, the current level at which the stapedial muscle reflex is elicited corresponds to the most comfortable current level for a cochlear implant patient.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

When neurons within the auditory nerves are activated by natural or artificial means, they generate pulses of electrical current called action potentials. The current produced by a single neuron is very small, but artificial electrical stimulation applied by, for example, a cochlear implant system, tends to recruit large numbers of neurons synchronously. This results in a compound action potential (CAP) that can be recorded electronically in the tissues surrounding the neurons, particularly in the fluid-filled cochlear ducts where the stimulating electrodes of a cochlear implant system are usually located. The amplitude of the compound action potential is approximately related to the number of auditory neurons that have been activated by the electrical stimulation.

The action potentials produced by auditory neurons are conducted to various relay nuclei of the brainstem, which transform the information into action potentials that are transmitted by other neurons to yet further nuclei and eventually to the perceptual centers in the cerebral cortex. The compound action potentials resulting from patterns of neural activity in these subsequent nuclei can also be recorded electronically, but they are very much weaker, less accessible, and more variable.

When the nerve signals finally arrive in the perceptual centers, they give rise to the conscious perception of sound and its apparent loudness. In normal hearing, the perceived loudness of sound depends on the amount of acoustic energy that is transmitted through the middle ear to the cochlea. The brain can control the amount of acoustic energy that reaches the cochlea by modulating the mechanical tension produced by two muscles in the middle ear: the stapedius muscle and the tensor tympani muscle. When contracted, the stapedius and tensor tympani muscles act as a dampening mechanism on the ossicular chain within the ear. In a normally functioning ear, contraction of the stapedius and tensor tympani muscles attenuates the vibration transmitted through the malleus, incus, and stapes to the oval window, so as to prevent overstimulation of the auditory system.

The mechanical tension of both the stapedius and tensor tympani muscles in response to a stimulus is bilateral and is commonly referred to as the stapedius muscle reflex or simply the stapedial reflex. The level of stimulation at which the stapedial reflex appears is associated approximately with the most comfortable current level for a particular person. It has been found that most people, even candidates for cochlear implants, have a stapedial reflex.

The presence of a stapedial muscle reflex reveals information about the afferent auditory system, the functions of the auditory brainstem, the integrity of the VIIth (facial) nerve, which innervates the stapedius muscle, and the functional status of the middle ear. Conventional methods of measuring the stapedial reflex are problematic and cumbersome and involve the use of a tympanometer. Tympanometry assesses middle ear status by measurement of acoustic impedance, which, as described previously, is associated with stapedial reflex. The tympanometer is a stand-alone device and its use involves the placement of a probe in the patient's ear. The probe and probe tip are sealed into the ear canal allowing the device to vary pressure in the ear canal while presenting an acoustic probe tone and making sound measurements in the ear canal. The patient must remain still and quiet as the pressure in the ear canal is varied. The tympanometer and cochlear implant must be connected and synchronized so that the tympanometer's measurements can be made coincident in time with the electrical stimulus used to elicit the stapedial reflex. The pressurization of the ear canal required in tympanometry sometimes results in discomfort and/or pain for the patient. Moreover, children must usually be sedated, which may interfere with the stapedial reflex.

Hence, a number of non-invasive systems and methods for measuring the stapedial reflex are described herein. It has been discovered that an indirect noninvasive measurement of the stapedial reflex is the related change in acoustic reflectance of the ear. As will be described below, a cochlear implant system may be configured to non-invasively measure a change in acoustic reflectance of the ear in response to an elicited stapedial reflex. The measured stapedial reflex may then be used to automatically determine the most comfortable current level for a particular patient.

To facilitate an understanding of the methods and systems described herein, an exemplary cochlear implant system will be described in connection with FIG. 1. Exemplary cochlear implant systems suitable for use as described herein include, but are not limited to, those disclosed in U.S. Pat. Nos. 4,400, 590; 4,532,930; 4,592,359; 4,947,844; 5,824,022; 6,219,580; 6,272,382; and 6,308,101. All of these listed patents are incorporated herein by reference in their respective entireties.

Figure 1:
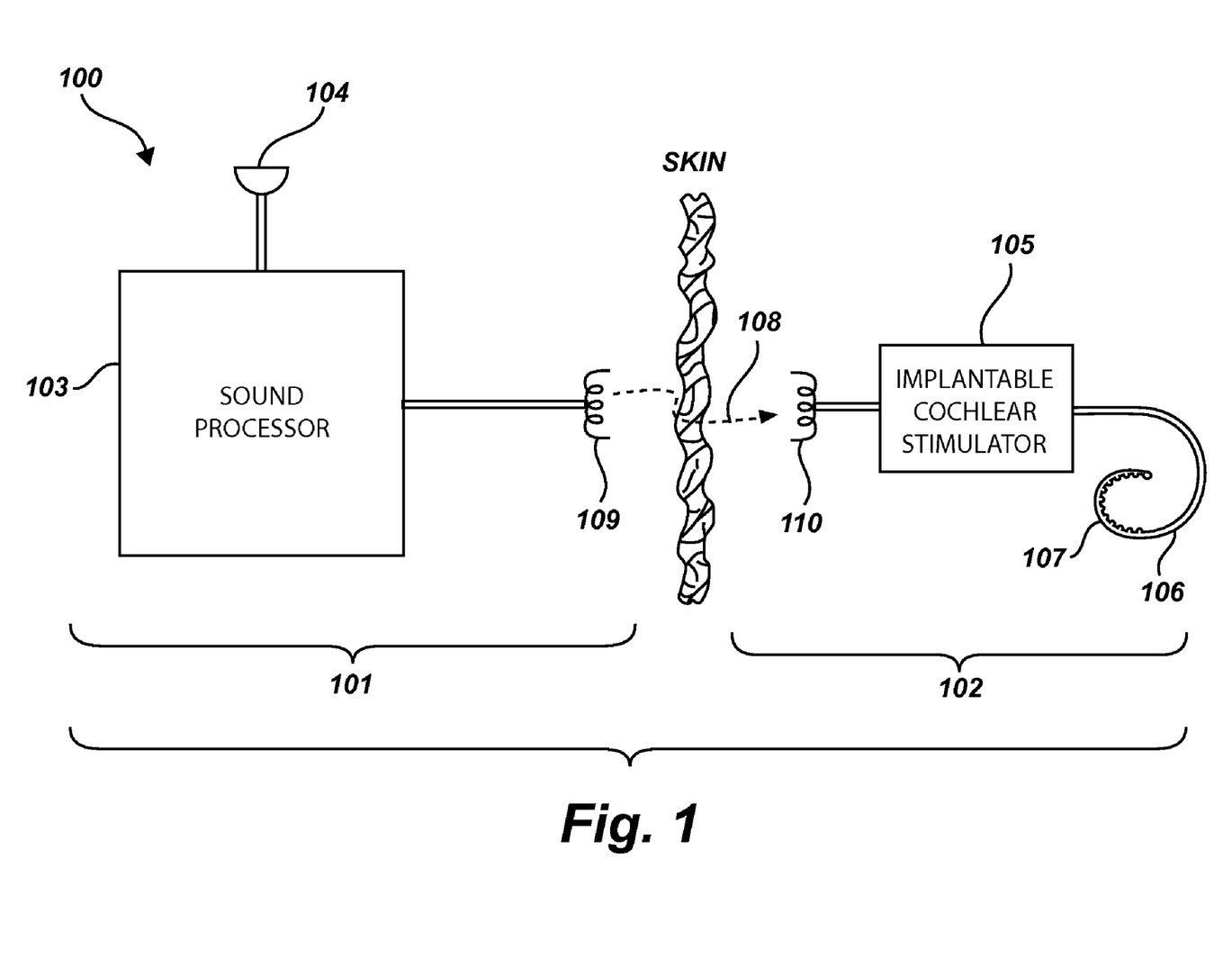
FIG. 1 illustrates an exemplary cochlear implant system according to principles described herein.

As shown in FIG. 1, the cochlear implant system 100 includes an external signal processor portion 101 and an implanted cochlear stimulation portion 102. The signal processor portion 101 may include a sound processor 103, a microphone 104, and/or additional circuitry as best serves a particular application. The cochlear stimulation portion 102 may include an implantable cochlear stimulator (ICS) 105, a lead 106 with a number of electrodes 107 disposed thereon, and/or additional circuitry as best serves a particular application. The components within the signal processor portion 101 and the cochlear stimulation portion 102 will be described in more detail below.

The microphone 104 of FIG. 1 is configured to sense acoustic signals and convert the sensed signals to corresponding electrical signals. The electrical signals are sent to the sound processor 103 over an electrical or other suitable link. Alternatively, the microphone 104 may be connected directly to, or integrated with, the sound processor 103.

The sound processor 103 may include any combination of hardware, software, and/or firmware as best serves a particular application. For example, the sound processor 103 may include one or more processors, digital signal processors (DSPs), filters, memory units, etc. In some examples, the sound processor 103 is configured to process the converted acoustic signals in accordance with a selected speech processing strategy to generate appropriate control signals or stimulation parameters for controlling the ICS 105. These stimulation parameters may specify or define the polarity, frequency, magnitude or intensity, location (i.e., which electrode pair or electrode group receive the stimulation current), and timing (i.e., when the stimulation current is to be applied to a particular electrode pair) of the stimulation current that is generated by the ICS 105.

In some examples, the sound processor 103 may include a behind-the-ear (BTE) unit configured to be positioned behind the ear. Additionally or alternatively, the sound processor 103 may include a portable speech processor (PSP) device or any other type of signal processor.

The lead 106 of FIG. 1 is adapted to be inserted within a duct of a patient's cochlea. As shown in FIG. 1, the lead 106 includes a multiplicity of electrodes 107 disposed along its length. The lead 106 may be substantially as shown and described in U.S. Pat. No. 4,819,647 or 6,129,753, each of which is incorporated herein by reference in its respective entirety. It will be recognized that any number of electrodes 107 may be disposed along the lead 106 as may best serve a particular application.

Each of the electrodes 107 is electrically coupled to the ICS 105. Electronic circuitry within the ICS 105 may therefore be configured to apply stimulation current to selected pairs or groups of electrodes 107 in accordance with a specified stimulation pattern controlled by the sound processor 103.

As mentioned, the ICS 105 and lead 106 may be implanted within the patient while the sound processor 103 and the microphone 104 are configured to be located outside the patient, e.g., behind the ear. Hence, the ICS 105 and the sound processor 103 may be transcutaneously coupled via a suitable data or communications link 108. The communications link 108 allows power and control signals to be sent from the sound processor 103 to the ICS 105. In some examples, data and status signals may also be sent from the ICS 105 to the sound processor 103.

The external and implantable portions of the cochlear implant system 100 may each include one or more coils configured to transmit and receive power and/or control signals via the data link 108. For example, the external portion of the cochlear implant system 100 may include an external coil 109 and the implantable portion of the cochlear implant system 100 may include an implantable coil 110. The external coil 109 and the implantable coil 110 may be inductively coupled to each other, thereby allowing data and power signals to be wirelessly transmitted therebetween.

Figure 2:
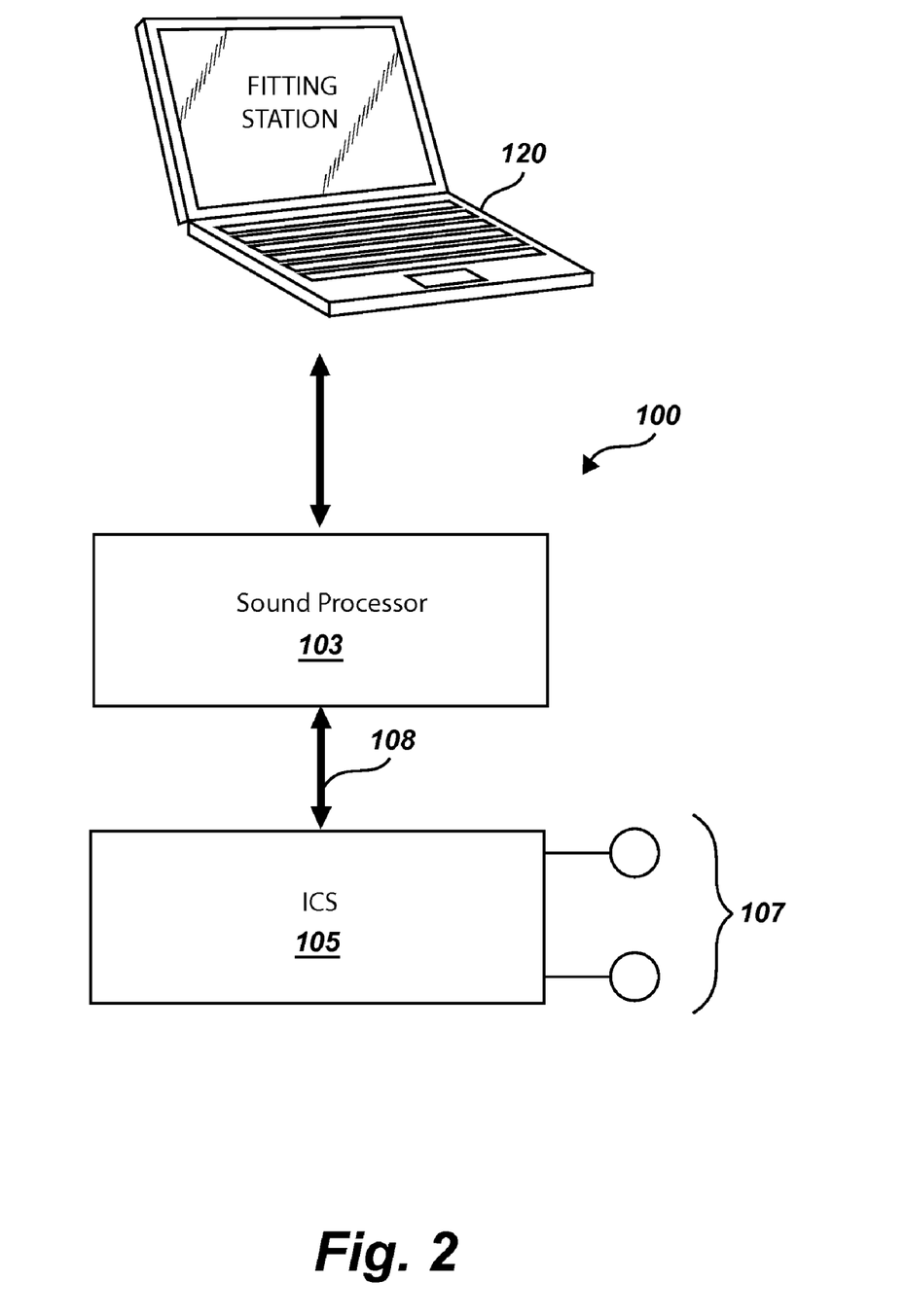
FIG. 2 illustrates fitting station communicatively coupled to a sound processor according to principles described herein.

FIG. 2 illustrates a functional block diagram of the cochlear implant system 100 wherein the sound processor 103 is communicatively coupled to a fitting station 120. The fitting station 120 may be used to program the sound processor 103 and may include any external device such as, but not limited to, a clinician's programming unit, a personal computer, a handheld device, a programming device, or the like. In some examples, a clinician may use the fitting station 120 to fit the cochlear implant system 100 to a particular patient.

As shown in FIG. 2, the sound processor 103 may be configured to transmit a number of control signals to the ICS 105 via the communications link 108. The control signals may be converted to analog signals by one or more digital-to-analog (D/A) converters, for example, and then applied to one or more driver circuits. In this manner, the ICS 105 may be configured to apply a stimulation current to one or more locations within the cochlea via one or more of the electrodes 107.

As mentioned, it has been discovered that an indirect non-invasive measurement of the stapedial reflex is the related change in acoustic reflectance of the ear. Hence, in some examples, the cochlear implant system 100 may be configured to automatically determine the optimal current levels for a particular patient by eliciting the stapedial reflex and measuring a corresponding change in the acoustic reflectance of the ear. It will be recognized that a corresponding change in admittance of the ear may additionally or alternatively be measured to determine the optimal current levels for a particular patient. However, for illustrative purposes only, it will be assumed in the examples herein that the acoustic reflectance is measured in order to determine when the stapedial reflex occurs.

Figure 3A:
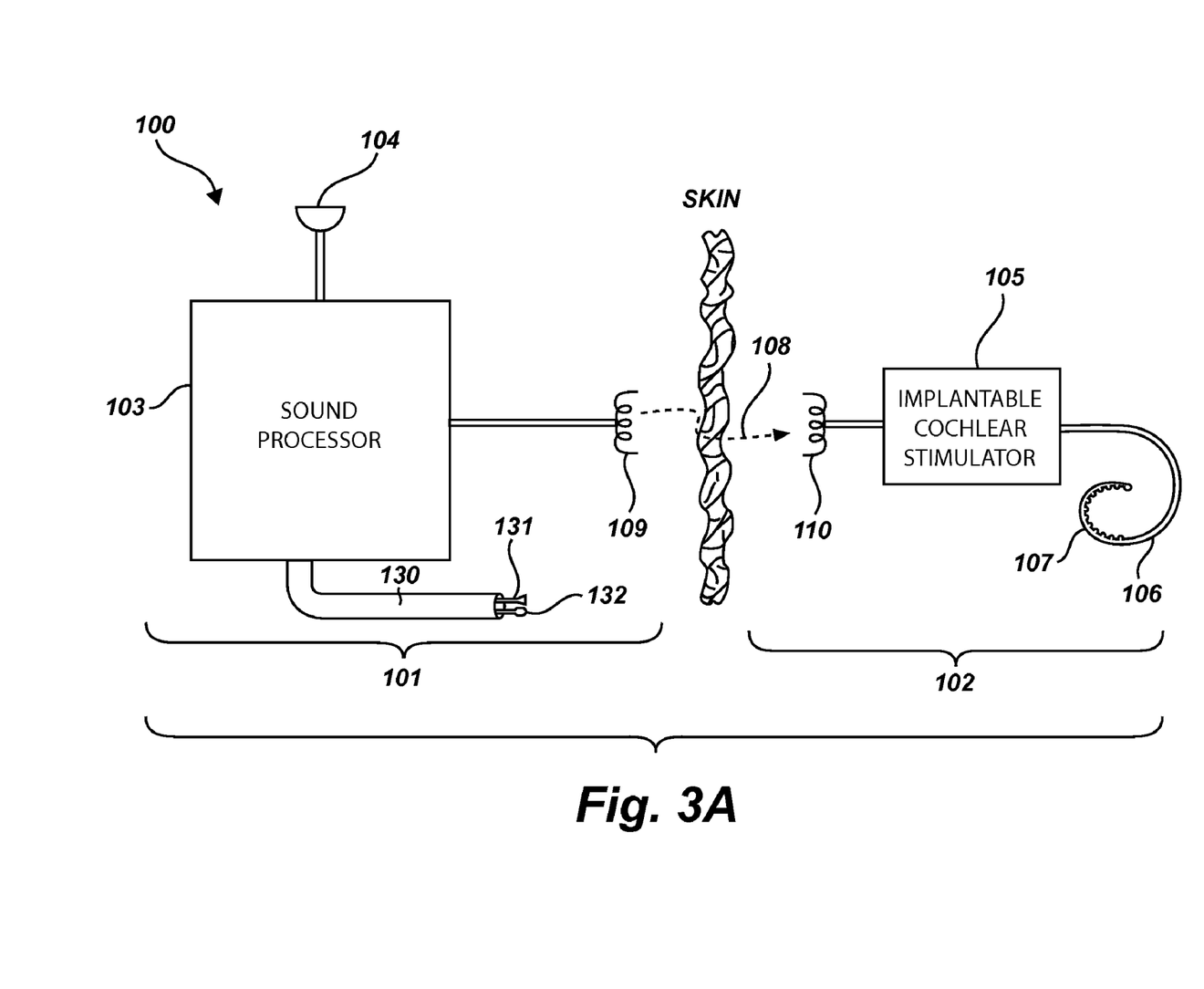
FIG. 3A illustrates an exemplary cochlear implant system with a probe coupled to the sound processor to facilitate measurement of acoustic reflectance according to principles described herein.

Hence, as shown in FIG. 3A, a probe 130 may coupled to the sound processor 103 to facilitate measurement of the acoustic reflectance. In some examples, the probe 130 may be removably coupled to the sound processor 103. Alternatively, the probe 130 may be permanently attached to the sound processor 103.

As shown in FIG. 3A, the probe 130 may include a speaker 131 and a microphone 132. As will be described in more detail below, the speaker 131 may be configured to emit one or more audio probe signals into the ear canal. The microphone 132 may be configured to sense an acoustic reflectance of the ear by sensing at least a portion of the probe signals that reflect or bounce back from the tympanic membrane (commonly referred to as the eardrum).

Figure 3B:
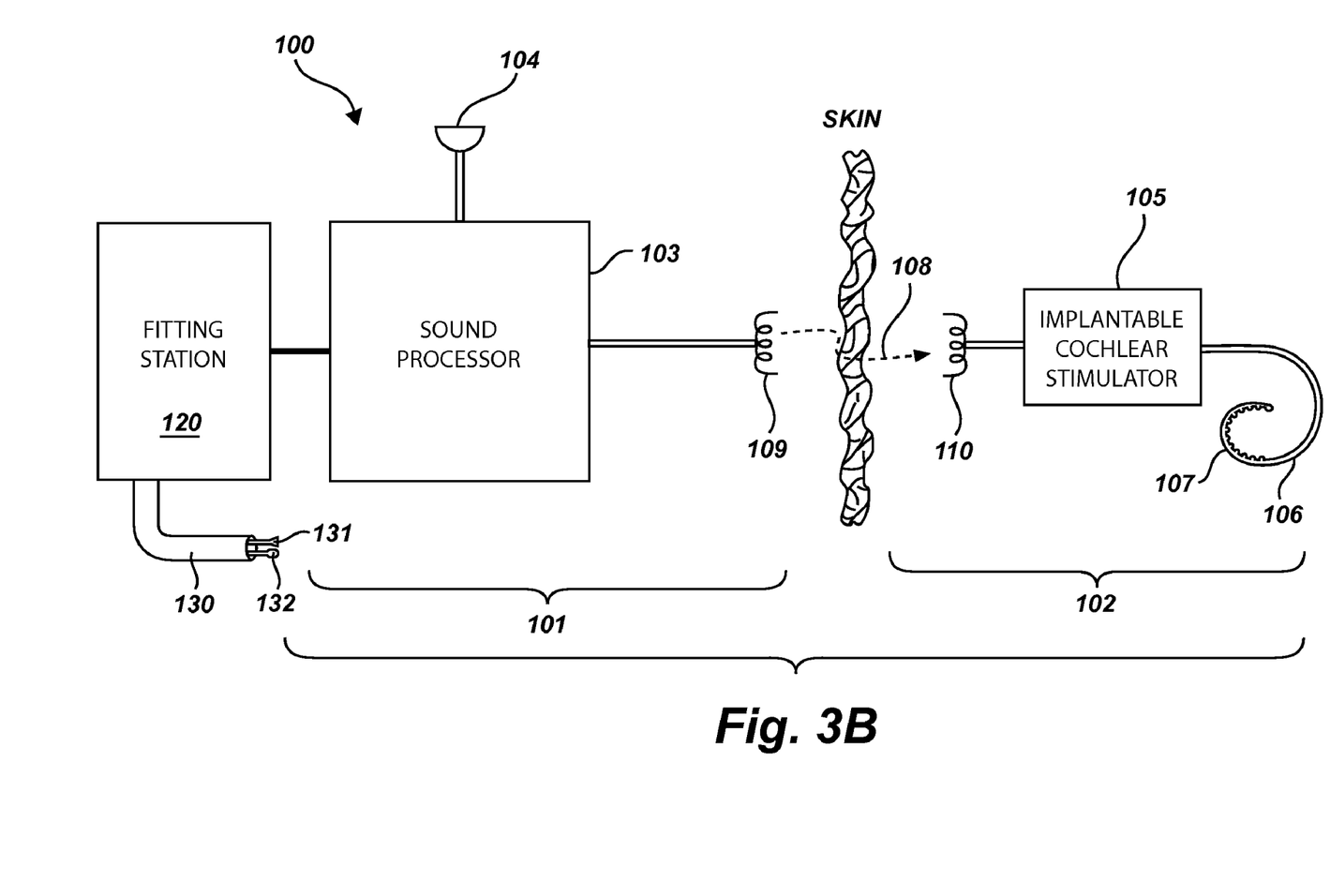
FIG. 3B shows an alternative configuration wherein the probe of FIG. 3A is coupled to a fitting station according to principles described herein.

It will be recognized that the probe 130 may alternatively be coupled to any other external device as may serve particular application. For example, FIG. 3B shows an alternative configuration wherein the probe 130 is coupled to a fitting station 120. In some examples, the probe 130 may be removably coupled to the fitting station 120. Alternatively, the probe 130 may be permanently attached to the fitting station 120.

In some alternative examples, the speaker 131 and microphone 132 are not included within the same probe 130. For example, the microphone 132 may be coupled to the sound processor 103 while the speaker 131 is coupled to the fitting station 120. However, for illustrative purposes, it will be assumed in the examples herein that the speaker 131 and microphone 132 are included within a single probe 130 that is configured to be coupled to the sound processor 103.

Figure 4:
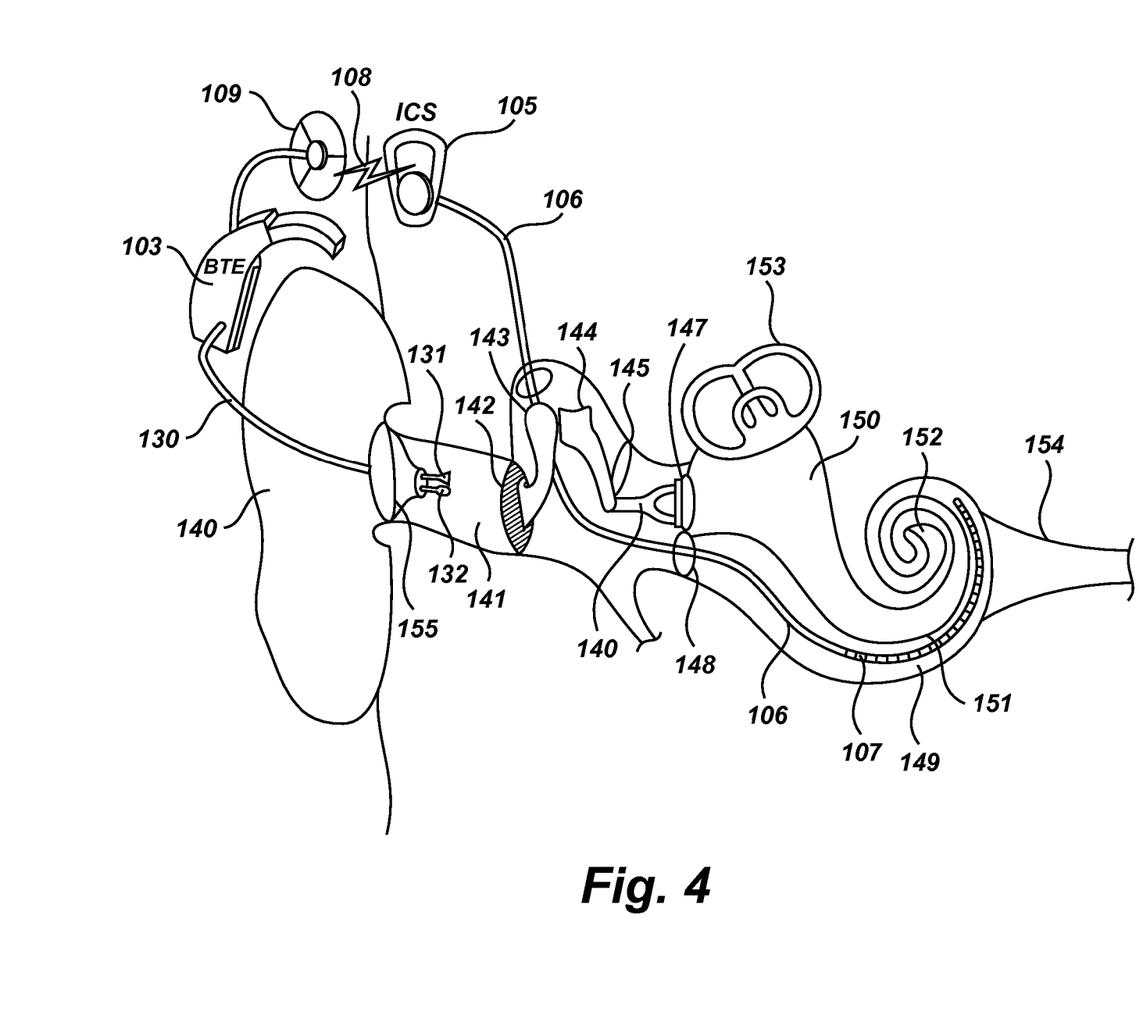
FIG. 4 illustrates an exemplary implementation of the cochlear implant system wherein the probe is inserted into the ear canal according to principles described herein.

FIG. 4 illustrates an exemplary implementation of the cochlear implant system 100 wherein the probe 130 is inserted into the ear canal. It will be recognized that the implementation shown in FIG. 4 is merely illustrative of the many different cochlear implant system configurations. For example, in some alternative implementations, the entire cochlear implant system may be implanted within the patient.

Various anatomical features of the ear are shown in FIG. 4. The major portions of the ear include the pinna 140, the ear canal 141, the tympanic membrane 142, the malleus 143, the incus 144, the stapedius muscle 145, the stapes 146, the oval window 147, the round window 148, various structures of the cochlea (e.g., the scala timpani 149, the scala vestibuli 150, the basilar membrane 151, the helicotrema 152, and the labyrinth 153), and the auditory nerve 154. In a normally functioning ear, the tympanic membrane 142 vibrates in response to ambient sound, and via the ossicular chain (which includes the malleus 143, the incus 144, and the stapes 146), the vibration is transferred to the oval window 147. The stapedius muscle 145 operates in the normal ear to contract and hence dampen mechanically the transmission of vibrations to the oval window 147.

As shown in FIG. 4, the sound processor 103 may be mounted behind the ear. The ICS 105 and lead 106 may be implanted within the patient. As shown in FIG. 4, the lead 106 may be inserted such that the electrodes 107 disposed thereon are in communication with the scala tympani 149 of the cochlea. The ICS 105 may communicate with the external coil 109, and hence the sound processor 103, via communications link 108. A microphone (not shown) may be coupled to the sound processor 103 and configured to provide sound signals thereto.

To facilitate measurement of the acoustic reflectance, the probe 130 may be inserted such that the speaker 131 and microphone 132 are contained within the ear canal 141. The probe 130 is shown to be coupled to the sound processor 103 in FIG. 4 for illustrative purposes. It will be recognized that the probe 130 may alternatively be coupled to the fitting station 120 and/or any other external device as may serve a particular application.

In some examples, a probe tip 155 may be used to occlude the opening of the ear canal 141. The probe tip 155 may be made out of any suitable material. For example, the probe tip may be made out of foam and allowed to expand after being inserted into the ear canal 141 so as to seal the ear canal 141.

Once the speaker 131 and microphone 132 have been adequately sealed within the ear canal 141, the sound processor 103 may measure the acoustic reflectance of the ear by applying an audio probe signal to the ear via the speaker 131. The audio probe signal may include any type of audio signal as best serves a particular application. An exemplary, but not exclusive, probe signal includes 40 millisecond (msec) electrical chirps with a bandwidth from 200 to 10,000 Hz. The overall sound pressure level (SPL) of the chirps may vary depending on the particular patient. It will be recognized that the aforementioned stimulation parameters are merely exemplary and may be varied for each particular patient.

Once applied within the ear canal 141, the probe signal travels through the ear canal 141 where at least a portion of the signal reflects off the tympanic membrane 51 and returns towards the microphone 132. The microphone 132 is configured to sense the reflected signal and transmit the acquired reflected sound data to the sound processor 103.

In some examples, the sound processor 103 includes one or more filters configured to remove biologic and system noise from the acquired sound data. For example, filters may include a 225 Hz 64 dB/octave) high pass filter or any other type of filter configured to remove biologic and system noise.

The filtered sound data may then be digitized with an A/D converter using any suitable sampling rate. For example, the sampling rate may be, but is not limited to, 24 kHz. The digitized sound data may then be stored by the sound processor 103 for data analysis. In some examples, as will be described in more detail below, the sound processor 103 may be configured to process the sound data acquired by the microphone 132 and computationally derive one or more acoustic reflectance measurements based on the sound data.

With the probe 130 configured as such to measure the acoustic reflectance of the patient's ear, the threshold current level needed to evoke a stapedial reflex may be determined by applying an electrical stimulation current with varying magnitude to the cochlea via the electrodes 107 and analyzing the resulting change in acoustic reflectance as measured by the probe 130. The stimulation current may be applied via any number of electrodes 107 as best serves a particular application. For example, the stimulation current may be applied via one electrode at a time. Alternatively, the stimulation current may be applied via multiple electrodes (e.g., four electrodes) at the same time. A number of exemplary methods of determining the threshold current level will now be described.

Figure 5:
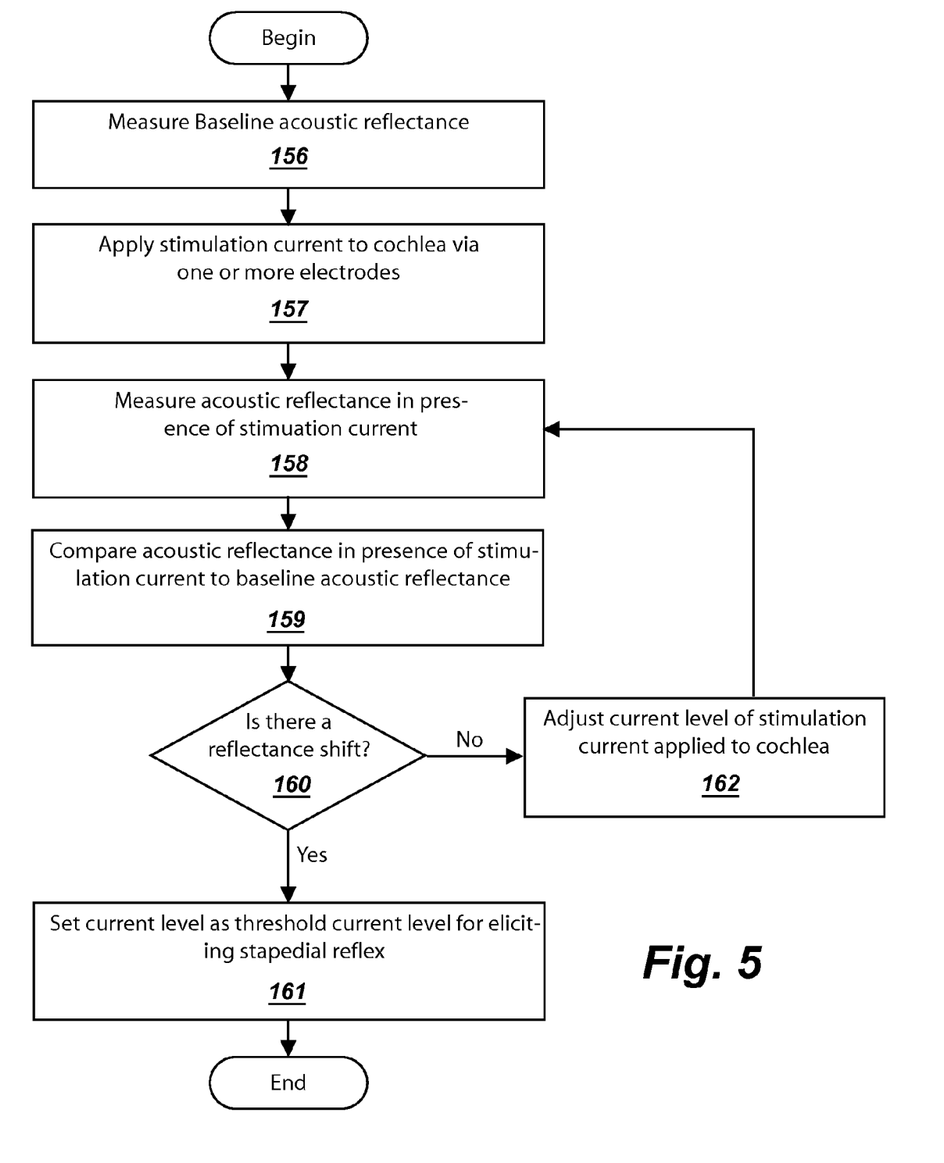
FIG. 5 is a flow chart illustrating an exemplary method of determining a threshold current level required to elicit a stapedial reflex according to principles described herein.

FIG. 5 is a flow chart illustrating an exemplary method of determining the threshold current level required to elicit a stapedial reflex. The steps shown in FIG. 5 are merely exemplary and may be modified, reordered, and/or added to as best serves a particular application.

As shown in FIG. 5, a baseline acoustic reflectance may first be measured (step 156). As used herein, the term "baseline acoustic reflectance" refers to an acoustic reflectance measurement obtained while the stapedial reflex is not being elicited. Hence, in some examples, the baseline acoustic reflectance is measured while the ICS 105 is not providing electrical stimulation to the cochlea.

The sound processor 103 may be configured to measure the baseline acoustic reflectance in a manner such as that described above. For example, the speaker 131 may apply an audio probe signal to the ear via the speaker 131 in the absence of electrical stimuli applied by the ICS 105. The audio probe signal may include, for example, a number of electrical chirps with a bandwidth from 200 to 10,000 Hz. However, the characteristics of the audio probe signal may vary as best serves a particular patient. The microphone 132 is configured to sense the sound signals that reflect from the tympanic membrane 51 and transmit the sound data to the sound processor 103. The sound processor 103 may then process the acquired sound data and determine the baseline acoustic reflectance using any suitable data processing technique. In configurations wherein the probe 130 is coupled to the fitting station 120, the fitting station 120 may be configured to measure the baseline acoustic reflectance.

In some examples, the baseline acoustic reflectance measurement is obtained by averaging multiple acoustic reflectance measurements in the absence of stimuli. However, it will be recognized that the measured baseline acoustic reflectance may include a single measured acoustic reflectance in some applications.

Figure 6:
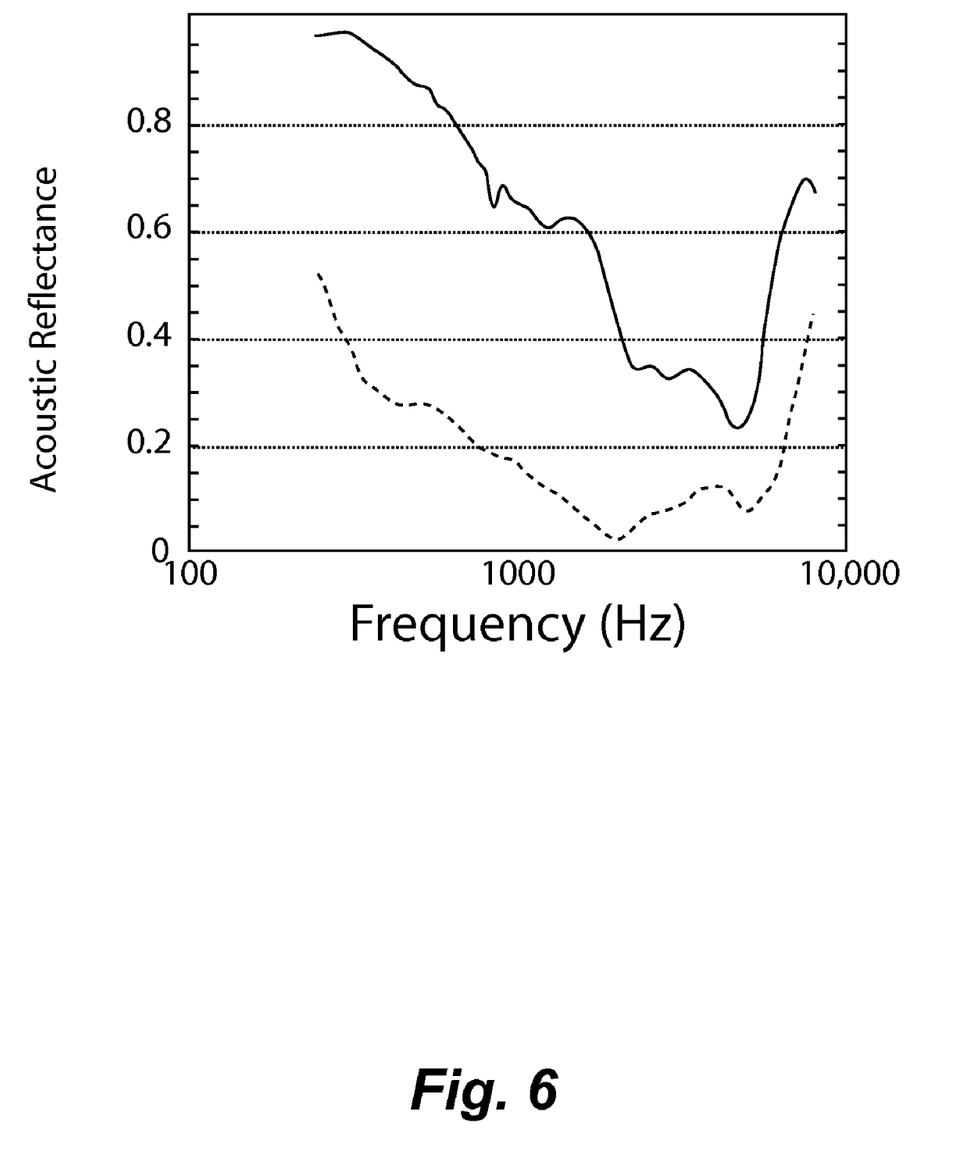
FIG. 6 illustrates an exemplary baseline acoustic reflectance measurement for an adult patient and an infant patient according to principles described herein.

FIG. 6 illustrates an exemplary baseline acoustic reflectance measurement for an adult patient (represented by the solid line) and an infant patient (represented by the dashed line). It will be recognized that the acoustic reflectance measurements shown in FIG. 6 are merely illustrative and that they may vary from patient to patient. As shown in FIG. 6, the reflectance value is near 1.0 in the low frequencies for the adult patient and decreases with frequency to a minimum near 4800 Hz. The response increases at higher frequencies to around 0.7 at 8000 Hz. Infant reflectance, as shown in FIG. 6 is typically lower than that of an adult.

Returning to FIG. 5, once the baseline acoustic reflectance measurement has been obtained, the ICS 105 may apply a stimulation current via one or more of the electrodes that are implanted within the cochlea (step 157). The acoustic reflectance is then measured in the presence of the stimulation current (step 158). The acoustic reflectance may be measured by the sound processor 103 and/or fitting station 120 as may serve a particular application. As will be described in more detail below, if the current level of the stimulation current is above a certain threshold, a corresponding change in the measured acoustic reflectance in comparison with the baseline acoustic reflectance will occur. In this manner, the current level corresponding to the most comfortable current level for the patient may be determined.

Hence, as shown in step 159, the measured acoustic reflectance in the presence of the stimulation current is then compared to the measured baseline acoustic reflectance. In some examples, the sound processor 103 is configured to perform the comparison. Additionally or alternatively, any other device (e.g., the fitting station 120 or the ICS 105) may be configured to perform the comparison. However, for illustrative purposes only, it will be assumed herein that the sound processor 103 is configured to perform the comparison.

The comparison performed by the sound processor 103 may vary as best serves a particular application. In some examples, the sound processor 103 may be configured to calculate a shift in reflectance between the baseline acoustic reflectance and the acoustic reflectance in the presence of the stimulation current. A shift in reflectance may be defined in this case as the acoustic reflectance in the presence of stimulation current minus the acoustic reflectance in the baseline condition.

If there is a reflectance shift above a pre-defined amount (Yes; step 160), the current level that resulted in that shift is set as the threshold current level for eliciting a stapedial reflex (step 161). To this end, the sound processor 103, fitting station 120, or other device may be configured to transmit data representative of a command to adjust the current level to the ICS 105. As will be described in more detail below, this current level may be used to optimally fit the cochlear implant system 100 to the patient. It will be recognized that the threshold current level may alternatively be set to be any other value related to the current level of the current level that causes the reflectance shift.

However, if it is determined that there is not a reflectance shift (No; step 160), the current level of the stimulation current is adjusted (step 162). For example, the current level of the stimulation current may be increased. The process of measuring the acoustic reflectance in the presence of the stimulation current and comparing the measured response to the baseline reflectance is repeated until the threshold current level for eliciting a stapedial reflex is determined.

Figure 7:
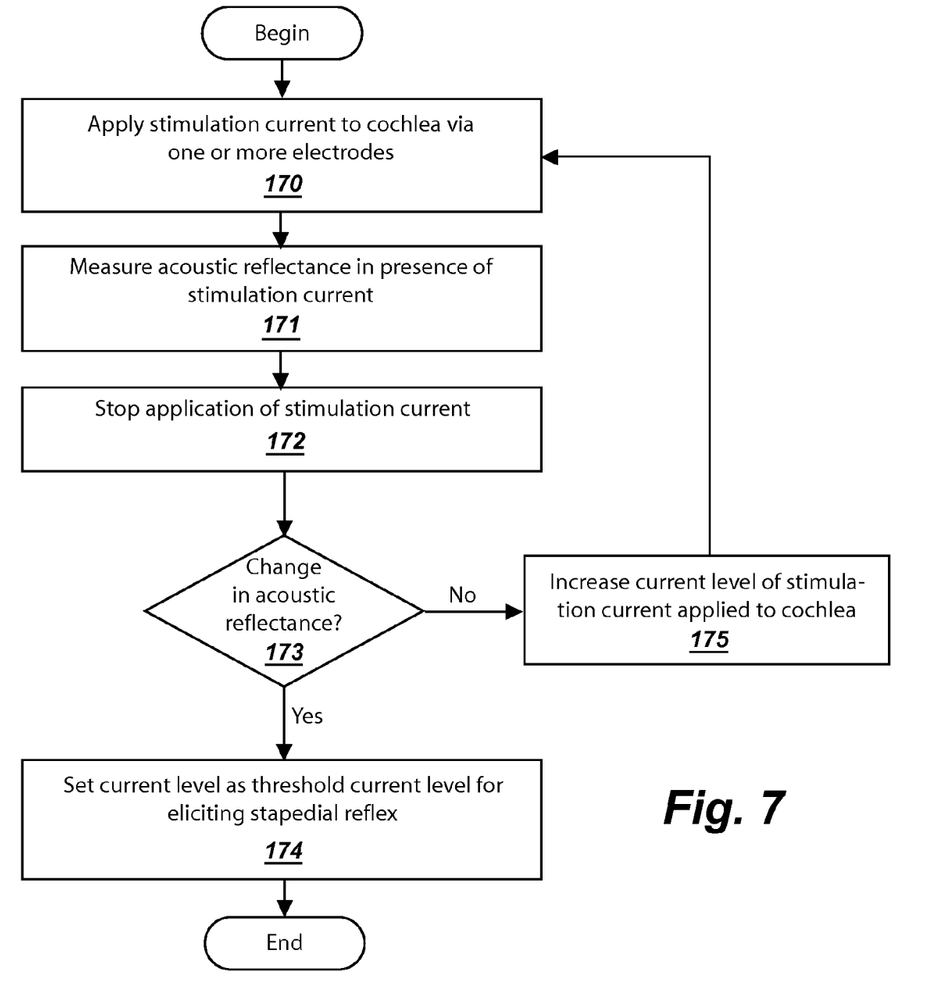
FIG. 7 is a flow chart illustrating another exemplary method of determining the threshold current level required to elicit a stapedial reflex according to principles described herein.

Another exemplary method of determining the threshold current level required to elicit a stapedial reflex is illustrated in FIG. 7. The steps shown in FIG. 7 are merely exemplary and may be modified, reordered, and/or added to as best serves a particular application.

As shown in FIG. 7, a stimulation current is first applied to the cochlea via one or more electrodes (step 170). The acoustic reflectance is then measured in the presence of the stimulation current (step 171). The acoustic reflectance may be measured in any of the ways described herein.

The application of the stimulation current is then stopped (step 172). However, the sound processor 103, fitting station 120, and/or other device continues to measure the acoustic reflectance. If a change in acoustic reflectance above a pre-defined threshold is detected by the sound processor 103 (Yes; step 173), it can be deduced that a stapedial reflex occurred in response to the application of the stimulation current. Hence, the current level of the stimulation current may then be set as the threshold current level for eliciting a stapedial reflex (step 174). As will be described in more detail below, this current level may be used to optimally fit the cochlear implant system 100 to the patient.

However, if a change in acoustic reflectance above the pre-defined threshold is not detected (No; step 173), it may be deduced that the stimulation current did not elicit a stapedial reflex. The current level of the stimulation current may then be increased (step 175) and steps 170-173 repeated until the change in acoustic reflectance indicates that a stapedial reflex has been elicited.

In some alternative examples, the current may be adjusted (e.g., decreased) and steps 170-173 of FIG. 7 repeated even if it is determined that a stapedial reflex has been elicited using a particular current level. For example, if an initial current level results in a stapedial reflex, the current level may be decreased in order to determine whether a lower current level will still result in a stapedial reflex.

Figure 8:
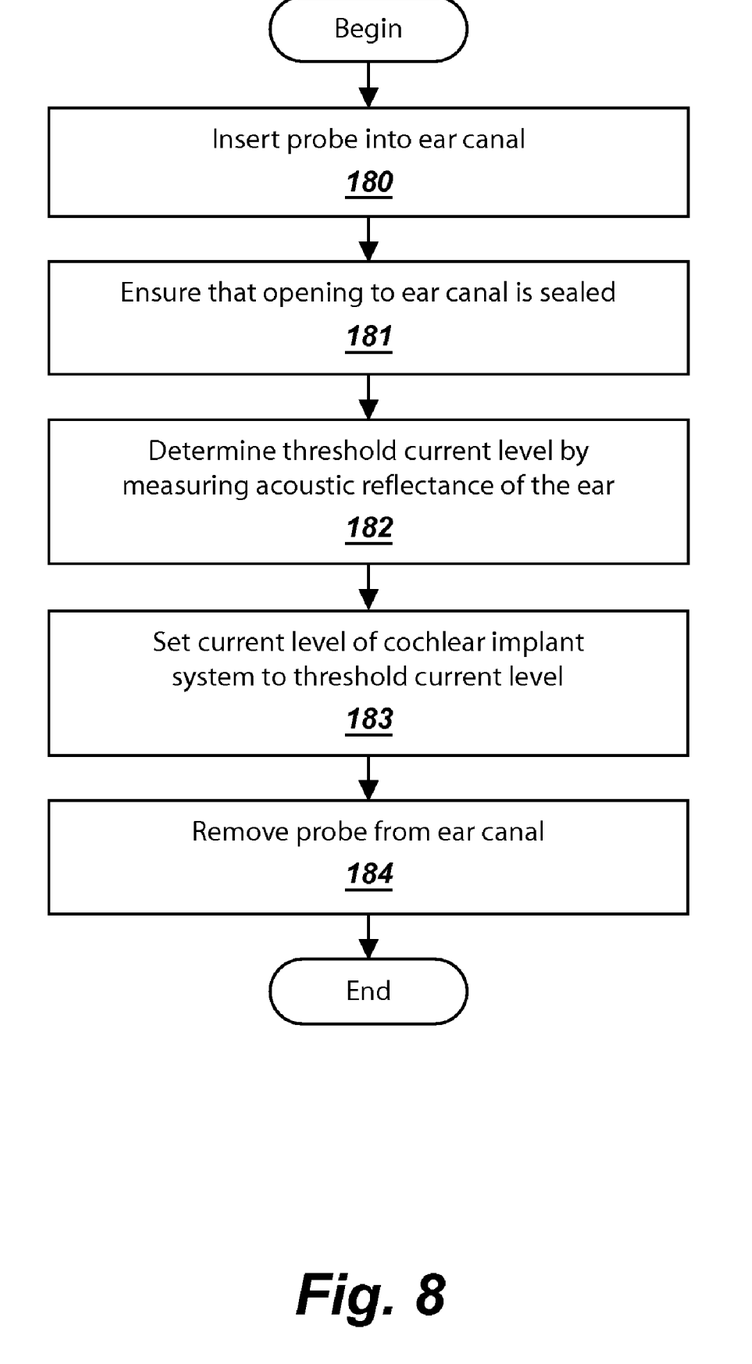
FIG. 8 is a flow chart illustrating an exemplary method of fitting a cochlear implant system to a particular patient according to principles described herein.

Hence, the systems and methods herein may be used to automatically fit a cochlear implant system 100 to a patient by automatically determining the current level of the stimulation current that corresponds to the most comfortable current level of a patient. For example, FIG. 8 is a flow chart illustrating an exemplary method of fitting a cochlear implant system 100 to a particular patient. The steps shown in FIG. 8 are merely exemplary and may be modified, reordered, and/or added to as best serves a particular application.

As shown in step 180, the probe 130 may be first implanted into the patient's ear canal. Tests may then be performed to ensure that the opening to the ear canal is properly sealed (step 181). Various acoustic reflectance measurements may then be performed to determine the threshold current level that evokes a stapedial reflex (step 182). The current level of the stimulation current applied via one or more of the electrodes may then be set to be equal to or based on the threshold current level (step 183). The probe may then be removed from the ear canal (step 184).

Because the stapedial reflex is bilateral, the probe 130 may be inserted into either or both ear canals. For example, the cochlear implant system 100 may be configured to apply an electrical stimulation current to the left cochlea and measure the acoustic response in the right ear canal and vice versa.

The preceding description has been presented only to illustrate and describe embodiments of the invention. It is not intended to be exhaustive or to limit the invention to any precise form disclosed. Many modifications and variations are possible in light of the above teaching.

What is claimed is:
1. A cochlear implant system comprising:
an implantable cochlear stimulator configured to be implanted within a patient and generate a stimulation current having an adjustable current level;

one or more electrodes communicatively coupled to said stimulator and configured to apply said stimulation current to one or more locations within an ear of said patient; and a probe configured to acquire sound data used to derive an acoustic reflectance of said ear, said probe comprising
a speaker configured to apply one or more probe signals within an ear canal of said patient; and
a microphone configured to detect said sound data;
wherein said sound data represents at least a portion of said probe signals that reflect off of a tympanic membrane of said patient, and
wherein said implantable cochlear stimulator is further configured to adjust said current level of said stimulation current until a change in said acoustic reflectance above a threshold is detected.

2. The system of claim 1, further comprising a fitting station communicatively coupled to said probe, wherein said fitting station is configured to:
process said sound data to derive said acoustic reflectance;
transmit data representative of a command to adjust said current level to said stimulator in accordance with said acoustic reflectance; and
detect said change in said acoustic reflectance.

3. The system of claim 2, wherein said fitting station is configured to detect said change in said acoustic reflectance by:
deriving a baseline acoustic reflectance while said implantable cochlear stimulator is not generating said stimulation current;
deriving an acoustic reflectance while said implantable stimulator is generating said stimulation current; and
comparing said acoustic reflectance derived while said implantable stimulator is generating said stimulation current to said baseline acoustic reflectance.

4. The system of claim 1, further comprising a sound processor communicatively coupled to said probe, wherein said sound processor is configured to:
process said sound data to derive said acoustic reflectance;
transmit data representative of a command to adjust said current level to said stimulator in accordance with said acoustic reflectance; and
detect said change in said acoustic reflectance.

5. The system of claim 4, wherein said sound processor is configured to detect said change in said acoustic reflectance by:
deriving a baseline acoustic reflectance while said implantable cochlear stimulator is not generating said stimulation current;
deriving an acoustic reflectance while said implantable stimulator is generating said stimulation current; and
comparing said acoustic reflectance derived while said implantable stimulator is generating said stimulation current to said baseline acoustic reflectance.

6. The system of claim 1, further comprising a probe tip configured to seal said speaker and said microphone within said ear canal.

7. The system of claim 1, wherein said one or more probe signals comprise at least one of a chirp signal and a noise signal.

8. The system of claim 1, wherein said change in said acoustic reflectance indicates a presence of a stapedial muscle reflex.

9. The system of claim 1, wherein said implantable cochlear stimulator is configured to set said current level of said stimulation current that results in said change in said acoustic reflectance as a threshold current level corresponding to a most comfortable current level of said patient.

10. A system comprising:
an implantable cochlear stimulator configured to be implanted within a patient and generate a stimulation current having an adjustable current level;
one or more electrodes communicatively coupled to said stimulator and configured to apply said stimulation current to one or more locations within an ear of said patient;
a sound processor communicatively coupled to said stimulator and configured to control said stimulator in accordance with one or more stimulation parameters;
a fitting station separate from and communicatively coupled to said sound processor; and
a probe communicatively coupled directly to said fitting station and configured to acquire sound data, said probe comprising
a speaker configured to apply one or more probe signals within an ear canal of said patient; and
a microphone configured to detect said sound data;
wherein said sound data represents at least a portion of said one or more probe signals that reflect off of a tympanic membrane of said patient;
wherein said fitting station is configured to derive an acoustic reflectance of said ear in accordance with said sound data; and
wherein said stimulator is configured to adjust said current level of said stimulation current until a change in said acoustic reflectance above a threshold is detected by said fitting station.

11. The system of claim 10, wherein said fitting station is configured to detect said change in said acoustic reflectance by:
deriving a baseline acoustic reflectance while said implantable cochlear stimulator is not generating said stimulation current;
deriving an acoustic reflectance while said implantable stimulator is generating said stimulation current; and
comparing said acoustic reflectance derived while said implantable stimulator is generating said stimulation current to said baseline acoustic reflectance.

12. The system of claim 10, further comprising a probe tip configured to seal said speaker and said microphone within said ear canal.

13. The system of claim 10, wherein said one or more probe signals comprise at least one of a chirp signal and a noise signal.

14. The system of claim 10, wherein said change in said acoustic reflectance indicates a presence of a stapedial muscle reflex.

15. The system of claim 10, wherein said implantable cochlear stimulator is configured to set said current level of said stimulation current that results in said change in said acoustic reflectance as a threshold current level corresponding to a most comfortable current level of said patient.

16. A method of determining a threshold current level required to evoke a stapedial muscle reflex within a patient, said method comprising:
applying a stimulation current having an adjustable current level to one or more locations within an ear of a patient;
measuring with a fitting station an acoustic reflectance of said ear during said application of said stimulation current by applying one or more probe signals with a speaker to an ear canal of said patient; and detecting sound data representing at least a portion of said probe signals that reflect off of a tympanic membrane of said patient with a microphone;

adjusting said current level of said stimulation current until a change in said acoustic reflectance above a threshold is detected; and setting said threshold current level to a value related to said current level of said stimulation current that causes said change in said acoustic reflectance.

17. The method of claim 16, wherein said change in said acoustic reflectance indicates a presence of a stapedial muscle reflex.

18. The system of claim 2, wherein the fitting station comprises a clinician's programming unit.

19. The system of claim 10, wherein the fitting station comprises a clinician's programming unit.

20. The method of claim 16, wherein the fitting station comprises a clinician's programming unit.

* * * * *